(12) United States Patent
Bender et al.

(10) Patent No.: US 7,207,505 B2
(45) Date of Patent: Apr. 24, 2007

(54) METHOD FOR PRODUCING SMALL GRANULES

(76) Inventors: Martin P. Bender, 1759 Cliiffside Ct., Naperville, IL (US) 60565; Donald P. Verbarg, 15625 Lisbon Center Rd., Newark, IL (US) 60541

( * ) Notice: Subject to any disclaimer, the term of this patent is extended or adjusted under 35 U.S.C. 154(b) by 104 days.

(21) Appl. No.: 10/860,937

(22) Filed: Jun. 4, 2004

(65) Prior Publication Data

US 2005/0269433 A1    Dec. 8, 2005

(51) Int. Cl.
*B02C 23/18*    (2006.01)

(52) U.S. Cl. .......................................... 241/21; 241/17

(58) Field of Classification Search .................. 241/17, 241/21

See application file for complete search history.

(56) References Cited

U.S. PATENT DOCUMENTS

| | | | | |
|---|---|---|---|---|
| 4,684,296 A | * | 8/1987 | Horii et al. ................. | 406/153 |
| 5,618,527 A | * | 4/1997 | Mendes et al. .......... | 424/78.01 |
| 5,780,055 A | * | 7/1998 | Habib et al. ................. | 424/464 |
| 6,039,275 A | * | 3/2000 | Slangen et al. ................ | 241/17 |
| 6,270,708 B1 | * | 8/2001 | Gurol ......................... | 264/117 |
| 6,440,965 B1 | * | 8/2002 | Kelley et al. ............. | 514/232.2 |
| 6,635,278 B1 | * | 10/2003 | Dahl et al. ................... | 424/465 |
| 6,845,793 B2 | * | 1/2005 | Ruffer et al. ................... | 141/7 |

* cited by examiner

*Primary Examiner*—Lowell A. Larson
*Assistant Examiner*—Jason Y. Pahng

(57) ABSTRACT

A method for quickly forming a high value powdered feed materials, particularly pharmaceuticals, into small, durable granules using known elements of process equipment, comprising the steps of mixing the feed materials with a wetting solution in a high shear mixer or granulator, partially drying the granulated mixture in a first drying means to a state of intermediate dryness, milling the partially dried granulated product in a stream of air to create small partially dried granules of the desired physical size, and drying the product in the second drying means to the desired final Loss On Drying (LOD) percentage of wetting solution. The milled product may be conveyed by vacuum from the milling step to the second drying means through a relatively long cylindrical transfer hose to create uniformly rounded granules.

7 Claims, 1 Drawing Sheet

METHOD FOR PRODUCING SMALL GRANULES

FIELD OF THE INVENTION

The present invention relates to a method for quickly and economically forming a wide variety of high value feed materials into small, durable granules. The preparation of such materials in granulated form is commonly required in the biotechnology, chemical, food, neutraceutical, pesticide, pharmaceutical and vitamin industries.

BACKGROUND OF THE INVENTION

Small, durable granules, often incorporating two or more ingredients, are desired by users in the aforementioned industries for a myriad of reasons. Products in flowable granular form are durable and easy to store, package and ship without deterioration or disintegration. Also they can be incorporated relatively easily into solid dosage forms for pharmaceutical, biotechnical, neutraceutical, vitamin and process prepared food use by further processing into both capsule and pressed tablet form.

It is well known that durable granules can be made in continuous or batch processes utilizing various prior art methods and process equipment. Examples of such basic prior art methods are disclosed by Tsujimoto U.S. Pat. No. 6,695,989 B1(Feb. 24, 2004) which describes a fluidized bed granulation chamber and method of operation, and by Key U.S. Pat. No. 5,582,638 B1 (Jun. 24, 2003) which describes a simple mechanical system using a roller and a perforate screen. However, these prior art methods are often highly labor-intensive and time-consuming, and provide an uneconomically low yield of granules with physical sizes within the desired range.

Other prior art methods for producing granules of pharmaceutical materials are described in the following US patents.

Katdare et al. U.S. Pat. No. 6,692,764 B2 (Feb. 17, 2004) discloses (cols. 2–3) a process of wet granulation for compounding pharmaceutical agents to be pressed into tablets. The disclosed process comprises forming a powder blend of active ingredient with diluents, wet grinding the mixture with water to form granules, drying the granules with heated air in a dryer (either fluid bed or tray type), milling the granules to a uniform size, adding and blending a disintegrant, adding and blending a lubricant, and finally compressing the lubricated granule into tablet form. The single milling step takes place only after the product has been dried to its final level of dryness. The process is described as relatively time-consuming, with each of the mixing, granulating drying steps variously taking 20 to 30 minutes, or even 24 hours for tray drying.

Gergely, et al. U.S. Pat. No. 6,645,529 B2 (Nov. 11, 2003) discloses a process of forming "instant" granules (cols. 3–4) in which a carrier material is wetted at least partially before being coated with an active substance, after which additional active substance and liquid are added, followed by drying, final milling, and sieving to desired particle size, with the drying being carried out in a vacuum mixer. The initial mixing step is followed by a single milling step, and then by a final single drying step in a vacuum mixer.

Qui, et al. U.S. Pat. No. 6,419,953 B1 (Jul. 16, 2002) discloses a process (cols. 4–5) involving milling and sieving a bulk drug, mixing it with polymer and excipients in a high shear mixer, and adding liquid to achieve granulation. This is followed by tray drying overnight in a single step. After mixing with lubricant, the dried product is pressed into tablets.

Asgharnejad et al. U.S. Pat. No. 6,123,964 (Sep. 26, 2000) discloses a wet granulation process (cols. 2–4) characterized by mixing powdered active ingredient with a two liquid diluents and a disintegrant in a mixer, wet granulating by adding a solution while mixing, drying the mixed granules in a single step for up to 24 hours, milling the dried granules to a uniform size, adding first a disintegrant and then a lubricant, and finally pressing into tablet form.

Khankari et al. U.S. Pat. No. 6,106,274 B 1(Apr. 24, 2001) describes as "common technique" a method of forming matrix-type particles (cols. 7–8) in which the active substance is spay dried with a solution of polymeric protective material, dried to a solid state in a single step, and then communited (milled) to form the desired particles.

Schobel U.S. Pat. No. 4,687,662 (Aug. 18, 1987) discloses a process for preparing a rapid-dissolving effervescent composition (cols. 7–8) in which a granulation is formed by dissolving a granulating agent in a solvent with the active substance, drying the granulation in a single step, sizing the dried granulation in a single step, and then mixing in an effervescent system to obtain a uniform mixture of granules.

SUMMARY OF THE INVENTION

It is therefore a principal object of the present invention to provide an improved method for forming high-value powdered materials into granulated form by utilizing known elements of process equipment in a specific and novel sequence of operations, thereby resulting in the efficient and expeditious formation of a high percentage of desired small, durable, granules. A related objective is to provide such a process having an improved yield of such granules within a pre-selected desired range of sizes compared to what has been achievable by traditional prior art methods of using the same or similar equipment.

As a result, and as a benefit of the method taught in this invention, the granulation process can be speeded up, often yielding a reduction of processing time of twofold or more, while at the same time producing a notably higher yield of granule particles within a pre-selected range of desired particle sizes.

BRIEF DESCRIPTION OF THE DRAWING

The preferred embodiment is described with references to the drawing, in which.

DETAILED DESCRIPTION OF THE PREFERRED EMBODIMENT

Figure 1:
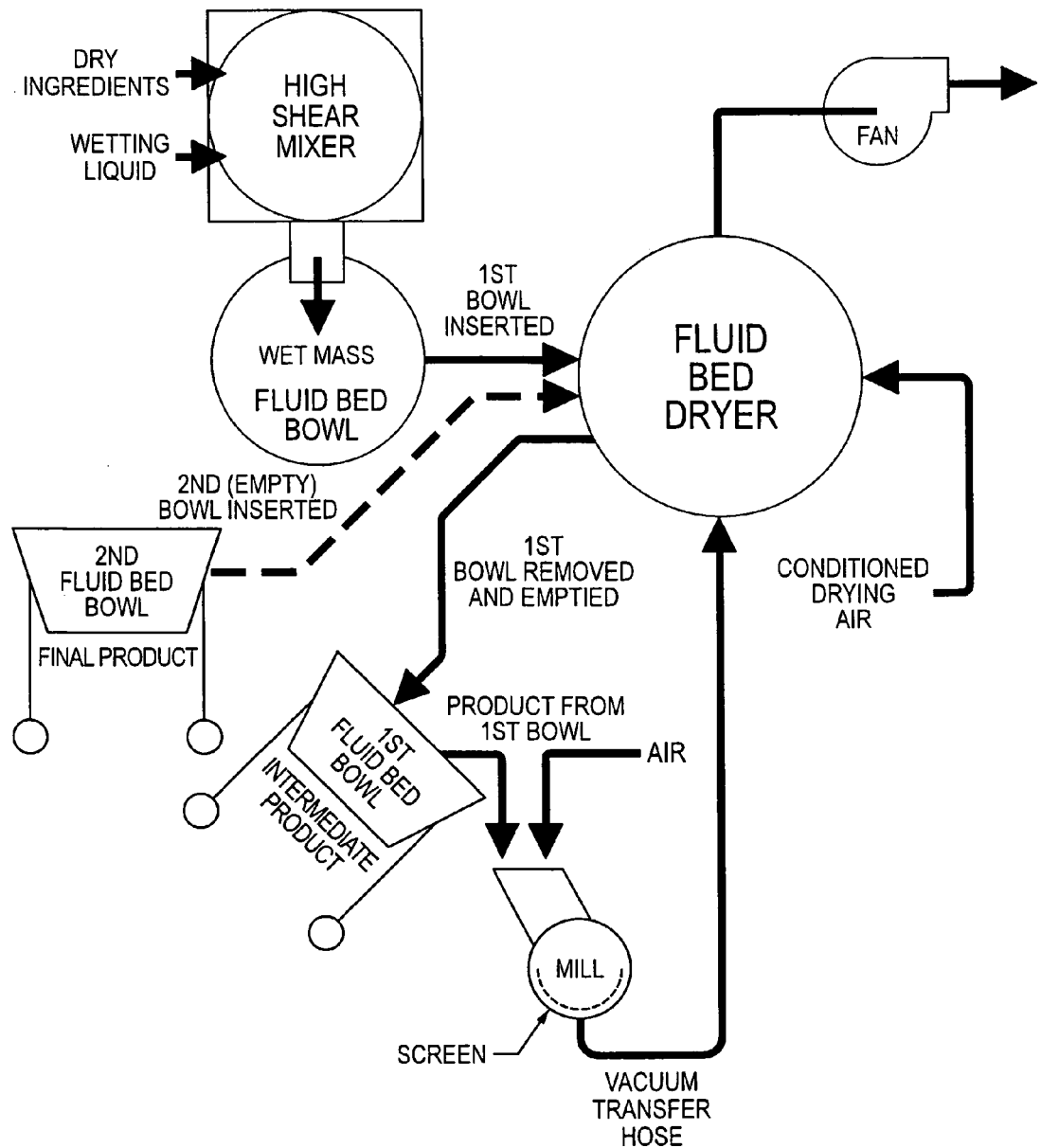
FIG. 1 is a schematic view depicting the relative organization and sequence of use of the several components used in performing the method of the present invention, with arrows indicating the sequence and flow of the process.

One or more dry ingredients in powder form, such as a pharmaceutical or mixture of pharmaceuticals which will comprise a major portion of a finished granular product, are loaded into a known high shear mixer or granulator such as the PHARMX® mixer manufactured by Fluid Air, Inc. of Aurora, Ill., USA. A suitable wetting liquid, such as water or an aqueous solution of other ingredients, is added. The ingredients are then mixed with the wetting solution in the high shear mixer wherein the characteristic mixing and chopping action of the device forms a thoroughly mixed, densified, wet granular mass.

The wet mass is then discharged into a fluid bed bowl of a batch-type fluid bed dryer such as the MAGNAFLO® dryer, also manufactured by Fluid Air, Inc. of Aurora, Ill. USA. In the fluid bed dryer the relatively wet product is subjected to a first drying step in which it is fluidized and partially dried by the fluidizing air stream to a state of intermediate dryness, but not to its final state of predetermined desired dryness.

At this point in the process, and according to a principal feature of the invention, the drying process is stopped and the bowl containing the partially dried intermediate product is removed from the fluid bed dryer and subjected to an intermediate milling step. In the illustrated example, this is done by removing the fluid bed bowl from the dryer, raising it, and inverting it to discharge its contents into a known size reduction mill such as the GRANUMILL®, also manufactured by Fluid Air, Inc. of Aurora, Ill. USA. In this step, the action of the mill rotor, assisted by sweeping the mill with a moving stream of air, creates an intermediate product consisting of small partially dried granules, which are separated and the mill's internal screen.

After this intermediate milling step, the still-wet product is conveyed back to the fluid bed dryer by a vacuum source connected to the discharge end of the mill for a second drying step in which the product is dried to the desired final Loss On Drying ("LOD") percentage of wetting solution. As shown in the drawing, the vacuum source is preferably a fan which is itself a component of the fluid bed dryer system. The transfer step back to the fluid bed dryer can be accomplished by any suitable means, but in the preferred embodiment it is done by means of a tubular transfer means, which in the illustrated embodiment is a relatively long cylindrical transfer hose utilizing the vacuum created by the fluid bed dryer's fan, such that the rolling action of the product as it passes along the wall of the hose "rounds off" the granules to a more spherical shape. Depending on the degree of rounding desired, the ratio of the length to diameter of the transfer hose is desirably between about 2 and about 200.

After being finish dried in the fluid bed dryer to the desired LOD percentage, the resulting product has been found to consist predominantly of a high proportion of desirable small, durable granules, resulting in a high yield of granules falling within a desired size range. Such a desired size range for the finished product can be selected from within an overall spectrum of possible sizes from about 74 microns to about 2000 microns.

The milled and finished dried granules may with the addition of a lubricant be incorporated directly into a pharmaceutical solid dosage form. Or alternatively, and most often preferred, the finish-dried granulated product can be passed through a separate screening machine to further sort out and eliminate granules falling outside of the desired preferred range. By selectively utilizing one or more screen sizes, the resulting product granules can be made highly uniform in size, compared to the product made with conventional granulation methods.

The desired particular physical characteristics of the granules, as well as the size and LOD of the granules, may be achieved by varying the powdered ingredients and liquid wetting agents and binding agents, or by varying one or more of the several possible configurations and process variables of the aforementioned equipment, which include (but are not limited to):

(1) The composition and quantity of dry ingredients, and composition and quantity of wetting liquid as supplied to the first mixing step;

(2) The length of time of the mixing step and speeds of the mixer impeller and chopper;

(3) The moisture content of the intermediate product upon discharge from the mixing step into the first fluid bed drying step;

(4) The degree of dryness (LOD) of the product upon discharge from the first fluid bed drying step into the size reduction step in the milling apparatus;

(5) In the important intermediate size reduction step, the hole size of the mill's internal screen, the speed of the mill rotor, the feed rate of the partially dried product into the mill inlet and the quantity of conveying air introduced along with the product into the mill inlet which quantity is regulated by the fluid bed dryer's fan which applies the vacuum to the mill discharge;

(6) The type, length and diameter of the vacuum hose used to transfer product from the milling apparatus to the fluid bed dryer for the second fluid bed drying step which determines the amount of "rounding off" of the milled particles into a more spherical shape;

(7) The quantity of the incoming drying air in the second fluid bed drying step and its temperature and moisture level;

(8) The length of drying time to achieve the desired LOD in the second fluid bed drying step; and (9) If used, the type of screener and the size of the holes in its one or more screens.

By adjusting some or all of the above variables one can optimize the method of the present invention and allow the resulting granulated product to be essentially duplicated from one batch to the next, therefore reliably assuring repeatable results. This is particularly advantageous in the manufacture of pharmaceutical products where provable consistent processing is extremely important and often legally required by applicable government regulations.

According to the invention, repeatable duplication of each of the above variables is achieved during production by the operator following the instructions contained in the product's "Master Batch Record", which would typically set forth the following:

First, the ingredients are selected, including both dry and liquid ingredients, in their relative quantities and proportions.

Second, the equipment must be configured and set up by the operator exactly the same for each batch, using, for example, the same size mill screen and the same vacuum transfer hose diameter and length.

Third, the equipment's operating parameters are selected. The operator selects a predetermined sequence of operations from a library of batch recipes, preferably using a known recipe based control system for the equipment to be used, such as FACTROL® manufactured by Fluid Air Inc of Aurora, Ill. and described in U.S. Pat. No. 5,576,946 (Nov. 19, 1996). This system incorporates a graphical interface control program using set-point controls which assure the repeatable duplication of each of the equipment's operating parameters, such as mixer impellor and chopper speeds, mill speed, and dryer gas flow. This proprietary control system also employs analog feedback control loops for monitoring and maintaining the specified equipment operating process variables such as flow, temperature and moisture content of the drying air.

Fourth, Process Analytical Control ("PAT") techniques may be incorporated into the equipment's control systems to adjust in real time the desired values of the operating parameters to compensate for changes experienced during the preceding steps. This involves such methods as controlling the milling step by passing a portion of the partially dried granulated product entering or exiting the mill through a laser diffraction instrument to provide feedback for controlling the speed of the mill.

Finally, the equipment control systems can incorporate other process analytical technology (PAT) techniques to determine process step end points, such as measuring the torque applied to the mixer shaft to achieve a desired density and moisture level of the wet mass, measuring the moisture level by viewing the product through a window in the fluid bed bowl using instrumentation means such as a Near Infrared Analyzer ("NIR") to end the first drying step, and measuring the temperature of the product in the fluid bed bowl to end the second drying step. This type of preprogrammed control of the pieces of equipment in the processing method of the present invention dictates that the equipment duplicate the entire process from one run to the next by assessing the density of the mixed wet mass and the dryness of the intermediate partially dried product as well as the final dryness of the finished small granules.

Four aspects of the procedure described above are particularly important in the practice of the processing method of the invention. The first important aspect lies in partially, but not completely, drying the wet intermediate mass to an optimal moisture content so that the resulting product will pass through the smallest possible mill screen orifice without (on the one hand) having the product revert to its original fine-powder state, or (on the other hand) being over-wet and thereby clogging the mill screen during the milling step, neither of which is desirable. The second important aspect in the practice of the invention is to select a proper hole size of the mill's internal screen to maximize the yield of particles in the desired range of sizes. The third important aspect in the practice of the invention is the introduction of air with product at the inlet of the mill via a vacuum source being applied to the discharge of the mill to assist in pushing/pulling the partially dried particles through the holes in the mill screen. The fourth important aspect in the practice of the invention is the type, diameter and length of the vacuum transfer hose as this determines the amount of rounding off of the particles into a more spherical shape.

It has been found that the key to achieving a high yield of small evenly-sized granules in the desired size range using the method described is to determine, through trial and error or otherwise, the optimum combination of the variables (1) through (9) above for obtaining the desired LOD of the partially dried material after the first fluid bed drying step, and the smallest usable mill screen hole size in the milling step that follows, just before the second and final fluid bed drying step. It has also been found through experience that while one might be able to achieve the desired granule size on certain products by just using a single drying step after wet milling, there are other products in which one cannot depart from the first fluid bed drying or pre-drying step which precedes the milling step, because to do so causes unacceptable clogging and plugging of the mill screen or creation of particles too large to reside in the specified range This is particularly true when yields are required having a high percentage of granules at the small end of the desired range of sizes, because without the pre-drying step, the product either contains too much moisture to pass through the size hole selected for the mill screen, or mill screen hole size must be so large to get the product through the hole that the resulting granules have an unacceptable size distribution with too many granules falling outside or at the large end the desired range of sizes.

The method of the present invention is therefore capable of yielding an high proportion of small, durable, granules falling within a desired predetermined range of sizes and moisture content (LOD), suitable for incorporation into tablets or capsules. By using the present method, such outstanding results can be repeatedly achieved with existing well-known high shear mixing, milling and fluid bed drying equipment.

We claim as our invention:

1. A novel method of rapidly and efficiently producing a finished granular product having a desired pre-selected range of particle sizes, shape, moisture content and flowability, said method yielding small, durable, rounded, flowable dry product granules having a high yield within a pre-selected range of particle sizes and being characterized by a step-wise process wherein the initial drying of a wet product mass is intentionally stopped at a predetermined intermediate non-final moisture content which provides for adequate plasticity of said mass to allow efficient intermediate size reduction of said granular mass to create uniform rounded granules falling predominately in the particle size range of 74 to 2000 microns, followed by final drying of said granules to said desired pre-selected range of particle sizes, shape, moisture content and flowability, said method comprising the following sequence of process steps in the order stated:

a) A first process step of mixing at least one dry powder ingredient with a liquid to produce a wet product mass; followed by
   b) A second process step of drying said wet product mass to create a wetted non-uniform intermediate product mass having said predetermined intentional state of intermediate non-final moisture content; followed by
   c) A third process step of milling said wetted non-uniform intermediate product mass by size reduction means including a mill having a screen with holes sized to produce a relatively uniform milled granular product having said predetermined intermediate non-final moisture content and a size distribution falling predominately between 74 to 2000 microns; followed by
   d) A fourth process step of finally drying substantially the whole of said relatively uniform milled granular product to produce a finished granular product having said desired pre-selected range of particle sizes, shape, moisture content and flowability.

2. The method of claim 1 in which said uniform milled granular product having said predetermined intermediate non-final moisture content and size distribution is transferred from said third process step to said fourth process step through a tubular transfer hose having a length and wall diameter selected such that wall contact during passage therethrough causes the granules of said uniform granular product to be rounded off into substantially spherical shapes.

3. The method of claim 2 in which said tubular transfer hose has a ratio of length to diameter of between about 2 and 200.

4. The method of claim 2 in which said wetted uniform milled granular product is transferred from said third process step to said fourth process step by vacuum means including a fluid bed dryer.

5. The method of claim 1 in which at least a portion of said uniform milled granular product is passed through instrumentation means for providing continuous monitoring of particle size distribution, and the feed rate of said third process step is adjusted responsive to said continuous particle size distribution monitoring to maintain an average particle size distribution within said pre-selected range of particle sizes prior to said fourth process step.

6. The method of claim 1 in which at least a portion of said uniform milled granular product from said third process step is passed through instrumentation means including a Near Infrared (NIR) Analyzer for providing continuous monitoring of its moisture content, and the feed rate of said third process step is adjusted responsive to said moisture content to maintain said predetermined intermediate non-final moisture content prior to said fourth process step.

7. The method of claims 1, 2 or 4 in which substantially the whole of said wetted non-uniform intermediate product mass, after being milled by said size reduction means, is drawn through said mill screen holes by the vacuum created by the fan of a fluid bed dryer.

* * * * *